United States Patent [19]
McCarthy et al.

[11] Patent Number: 5,378,693
[45] Date of Patent: Jan. 3, 1995

[54] 2'-HALOMETHYLIDENE CYTIDINE, URIDINE AND GUANOSINE COMPOUNDS AND THEIR PHARMACEUTICAL COMPOSITIONS

[75] Inventors: James R. McCarthy, West Chester; Michael L. Edwards, Cincinnati; Donald P. Matthews, West Chester, all of Ohio

[73] Assignee: Merrell Dow Pharmaceuticals Inc., Cincinnati, Ohio

[21] Appl. No.: 113,505

[22] Filed: Aug. 27, 1993

Related U.S. Application Data

[63] Continuation of Ser. No. 563,470, Aug. 7, 1990, abandoned, which is a continuation-in-part of Ser. No. 271,479, Nov. 15, 1988, abandoned.

[51] Int. Cl.$^6$ ................ C07H 19/073; C07H 19/173
[52] U.S. Cl. ...................... 514/45; 514/49; 514/50; 536/27.13; 536/27.14; 536/27.81; 536/28.2; 536/25.5; 536/28.53
[58] Field of Search ............... 536/27.14, 27.81, 28.2, 536/28.5, 28.53, 4.1, 29.2, 27.13

[56] References Cited

U.S. PATENT DOCUMENTS 3,472,837 10/1969 Verheyden et al. ............ 536/27.14

FOREIGN PATENT DOCUMENTS 0310673 4/1989 European Pat. Off. ......... 536/27.14
1113851 5/1968 United Kingdom ............ 536/27.14

OTHER PUBLICATIONS

De Clercq, "S-Adenosylhomocysteine Hydrolase Inhibitors as Broad Spectrum Antiviral Agents", *Biochemical Pharmacology*, 36(16), 2567–2575 (1987).

Ferrier, "4',5'-Unsaturated, Cyclic Compounds", *Adv. Carbohydrate Chem.*, 24, 250–251 (1969).

Fukukawa et al., "Synthesis of 2'(R)-Substituted Neplanocin A's (Nucleosides and Nucleotides XXXVII)," *Chem. Pharm. Bull.*, 29, 597–600 (1981).

Katritzky et al., *Comprehensive Heterocyclic Chemistry*, vol. 5, Pergamon Press, New York, 1984, see p. 603.

Takenuki et al., "Design Synthesis, and Antineoplastic Activity of 2'-Deoxy-2'-methylidenecytidine," *J. Med. Chem.*, 31(6), 1063–1064 (1988).

Matsuda et al., "Alkyl Addition Reaction of Pyrimidine 2'-Ketonucleosides:Synthesis of 2'-Branched-Chain Sugar Pyrimidine Nucleosides (Nucleosides and Nucleotides LXXXI)", *Chem. Pharm. Bull.*, 36(3), 945–953 (1988).

Hansske et al., "Nucleic Acid Related Compounds, 43. A Convenient Procedure for the Synthesis of 2' and 3'-Ketonucleosides," *Tett. Lett.*, 24(15), 1589–1592 (1983).

Hansske et al., "2' and 3'-Ketonucleosides and Their Arabino and Xylo Reduction Products," *Tetrahedron*, 40(1), 125–135 (1984).

*Primary Examiner*—John W. Rollins
*Assistant Examiner*—L. Eric Crane
*Attorney, Agent, or Firm*—Louis J. Wille

[57] ABSTRACT

This invention relates to certain novel 2'-halomethylidene, 2'-ethenylidene and 2'-ethynyl cytidine, uridine and guanosine derivatives, and compositions thereof, which are useful in the treatment of patients afflicted with neoplastic or viral disease states.

14 Claims, No Drawings

2'-HALOMETHYLIDENE CYTIDINE, URIDINE AND GUANOSINE COMPOUNDS AND THEIR PHARMACEUTICAL COMPOSITIONS

CROSS-REFERENCE TO RELATED APPLICATION

This is a continuation of U.S. patent application Ser. No. 07/563,470, filed Aug. 7, 1990, now abandoned, which is a continuation-in-part of U.S. patent application Ser. No. 07/271,479, filed Nov. 15, 1988 (now abandoned).

SUMMARY OF THE INVENTION

The present invention relates to novel 2'-halomethylidene, 2'-ethenylidene and 2'-ethynyl cytidine, uridine and guanosine derivatives which are useful as in the treatment of carcinoma.

The present invention provides novel 2'-halomethylidene derivatives of the formula (1)

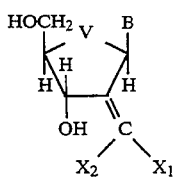

wherein
V is oxy, methylene, or thio,
$X_1$ and $X_2$ are each independently hydrogen or halogen, with the proviso that at least one of $X_1$ and $X_2$ is halogen,
B is a radical of the formula

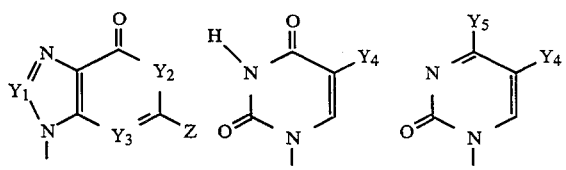

wherein $Y_1$ is nitrogen, a CH group, a CCl group, a CBr group or a $CNH_2$ group; $Y_2$ and $Y_3$ are each independently nitrogen or a CH group; $Y_4$ is hydrogen, $C_1$–$C_4$ alkyl, $C_1$–$C_4$ alkoxy or halogen; $Y_5$ is amino or $C_1$–$C_4$ alkoxy; and Z is hydrogen, halogen, or $NH_2$;
or a pharmaceutically acceptable salt thereof.

In addition, the present invention also provides novel 2'-ethenylidene derivatives of the formula (1a)

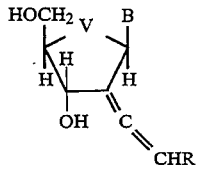

wherein
R is hydrogen or $C_1$–$C_4$ alkyl, and V and B are as previously defined;
or a pharmaceutically acceptable salt thereof.

Furthermore, the present invention provides novel 2'-ethynyl derivatives of the formula (1b)

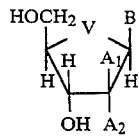

wherein
$A_1$ and $A_2$ are each independently hydrogen or a —C≡CR group, with the proviso that where $A_1$ is hydrogen $A_2$ is a —C≡CR group, and where $A_1$ is a —C≡CR group $A_2$ is hydrogen, and V, R and B are as previously defined;
or a pharmaceutically acceptable salt thereof.

The present invention also provides novel 2'-arylsulfonylmethylidene derivatives of the formula (6)

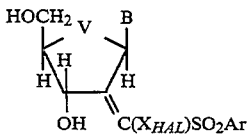

wherein Ar is a $C_6$–$C_{12}$ aryl group, $X_{HAL}$ is halogen, and V and B are as previously defined. The compounds of formula (6) are useful as chemical intermediates in the synthesis of compounds of formula (1) wherein one of $X_1$ or $X_2$ is hydrogen.

DETAILED DESCRIPTION OF THE INVENTION

As used herein, the term "halogen" or "halo-" refers to a fluorine, chlorine, bromine, or iodine atom and the term "nitrogen" refers to a trivalent nitrogen atom attached to two radicals. The term "$C_1$–$C_4$ alkyl" refers to a saturated straight or branched chain hydrocarbyl radical of one to four carbon atoms and includes methyl, ethyl, propyl, isopropyl, n-butyl, isobutyl, tertiary butyl and the like.

The term "$C_6$–$C_{12}$ aryl group" refers to an aromatic hydrocarbon of from about 6 to about 12 carbon atoms such as phenyl, naphtyl or phenyl($C_1$–$C_4$)alkyl groups wherein said groups are optionally substituted with one, two or three substituents selected from the group consisting of $C_1$–$C_4$ alkyl, halo-substituted $C_1$–$C_4$ alkyl, halogen or $C_1$–$C_4$ alkoxy. The term "phenyl($C_1$–$C_4$)alkyl" refers to a phenyl group substituted with a $C_1$–$C_4$ alkyl including phenylmethyl and phenethyl groups. The term "halo-substituted $C_1$–$C_4$ alkyl" refers to a $C_1$–$C_4$ alkyl group substituted with one to three halogen atoms including fluorine and chlorine. The term "$C_1$–$C_4$ alkoxy" refers to a $C_1$–$C_4$ alkyl bearing an oxy group and includes methoxy, ethoxy, propoxy, butoxy and the like.

The 2'-halomethylidene, 2'-ethenylidene and 2'-ethynyl derivatives of formula (1), (1a) or (1b) can be prepared by utilizing procedures and techniques well known and appreciated by one of ordinary skill in the art.

A general synthetic procedure for the preparation of compounds of formula (1) wherein both $X_1$ and $X_2$ are halogen is set forth in Scheme A. In the following schemes all substituents, unless otherwise indicated, are as previously defined. In addition, the term "φ" refers to a phenyl group; the term "$X_{HAL}$" refers to a halogen atom; the term "LP=" indicates a phosphorus ylide moiety [for example, a difluoromethylidene phosphonate ylide can have the formula $(\phi)_2P(O)=C(F)_2$ which can thus be abbreviated as $LP=C(F)_2]$.

Scheme A

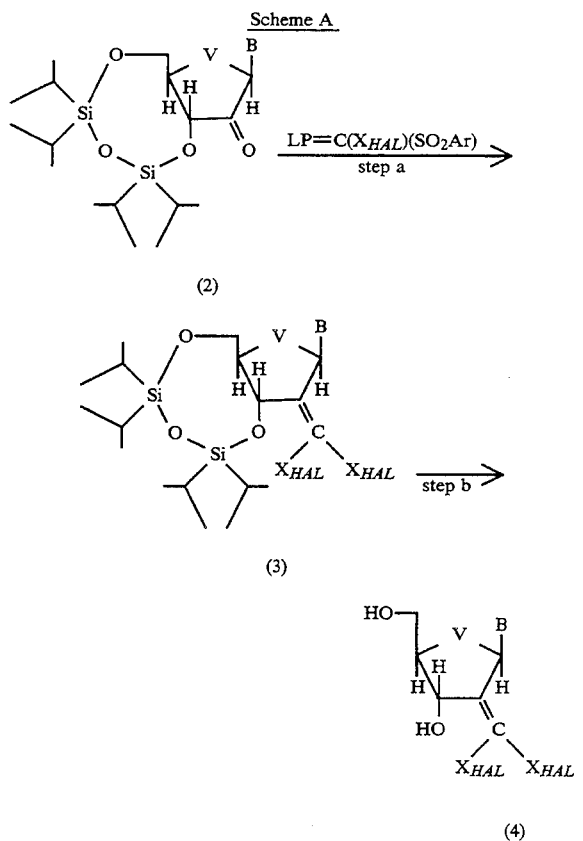

In step a, the ketone derivative (2), for example, 4-ethoxy-1-[(3,5-O-tetraisopropyldisiloxan-1,3-diyl)-β-D-erythropentofuran-2-keto-osyl]-2(1H)-pyrimidone, can be reacted in a Wittig type reaction with a dihalomethylidene phosphorus ylide, to yield the corresponding 2-dihalomethylidene substituted derivative (3), for example, 4-ethoxy-1-[(3,5-O-tetraisopropyldisiloxan-1,3-diyl)-β-D-erythro-pentofuran-2-difluoromethylidene-osyl]-2(1H)-pyrimidone.

Phosphorus ylides can be prepared according to procedures which are well known and appreciated in the art of chemistry such as those described by J. March in "Advanced Organic Chemistry: Reactions, Mechanisms and Structure", McGraw-Hill Book Company, 702–10 (1968). For example, a phosphorane ylide can be prepared by treatment of an appropriate phosphorane or phosphonate derivative with an appropriate base. A wide variety of bases can be used including alkoxides and organometallics, such as alkyllithium or lithium dialkylamide. When a compound of formula (1) is desired wherein both $X_1$ and $X_2$ are halogen, a dihalomethylidene phosphorus ylide is utilized in step a.

Appropriate phosphoranes or phosphonates can be prepared by addition of phosphines or phosphine oxides, such as trialkylphosphine, triarylphosphine (including triphenylphosphine) and diarylphosphine oxide (including diphenylphosphine oxide), to the appropriate di- or tri-halomethane derivative. The appropriate phosphorane or phosphonate is converted to the corresponding phosphorus ylide by treating the phosphorane or phosphonate with base. This can be accomplished by carrying out the preparation of the phosphorane or phosphonate in the presence of an appropriate base.

When a compound of formula (1) is desired wherein both $X_1$ and $X_2$ are halogen, the appropriate ketone (2) can be reacted with a dihalomethylidene phosphorus ylide, prepared by reacting a phosphine or phosphine oxide with a trihalomethane in the presence of base.

More specifically, when a compound of formula (1) is desired wherein both $X_1$ and $X_2$ are fluorine, the appropriate ketone (2) is reacted with a difluoromethylidene phosphorus ylide, prepared by reacting a phosphine or phosphine oxide (such as diphenylphosphine oxide) with a difluorohalomethane (such as difluorochloromethane) in the presence of base (such as butyllithium).

In step b, the tetraisopropyldisiloxan blocking group of (3) is removed, according to conventional procedures and techniques well known and appreciated in the art, to yield the de-blocked dihalomethylidene derivative (4). The tetraisopropyldisiloxan blocking group can be removed by reacting (3) with a fluoride anion or acid to effectively remove the blocking group without degradation of the desired product. For example, tetrabutylammonium fluoride, dilute acetic acid or dilute hydrochloric acid can be used.

Where a 4-alkoxy-substituted pyrimidone, such as the 4-ethoxy-substituted pyrimidone, is utilized as the starting material (2) for step a, the 4-alkoxy moiety of the pyrimidone base can be converted, in step b, to the 4-keto moiety to yield the corresponding uridine or thymidine derivative (4) or it can be converted to the 4-amino moiety to yield the corresponding cytidine derivative (4). These reactions can be effected according to procedures well known and appreciated in the art of chemistry. For example, where a uridine or thymidine derivative is desired, the 4-ethoxy-dihalomethylidine derivative of (4) can be treated with a base, such as sodium hydroxide, to convert the 4-ethoxy moiety to a 4-keto moiety in a nucleophilic displacement/enolization reaction. Where a cytidine derivative is desired, the 4-ethoxy-dihalomethylidine derivative of (4) can be reacted with methanolic ammonia to effect the substitution of an $NH_2$ group for the 4-ethoxy moiety.

The following example presents a typical synthesis as described by Scheme A. This example is understood to be illustrative only and is not intended to limit the scope of the present invention in any way. As used herein, the following terms have the meanings as indicated below: "L" refers to liters; "g" refers to grams; "mol" refers to moles; "mL" refers to milliliters; "mg" refers to milligrams; "mmol" refers to millimoles; "° C." refers to degrees Celsius; "mp" refers to melting point; "Hz" refers to hertz; "DMF" refers to N,N-dimethylformamide; "M" refers to molar concentration; "DMSO" refers to dimethylsulfoxide; "THF" refers to tetrahydrofuran; "AIBN" refers to 2,2'-azobisisobutyronitrile.

EXAMPLE 1

2'-DEOXY-2'-DIFLUOROMETHYLIDENECYTI-DINE

Step a: 4-Ethoxy-1-[(3,5-O-tetraisopyldisiloxan-1,3-diyl)-β-D-erythro-pentofuran-2-(difluoromethylidene)osyl]-2(1H)-pyrimidone Prepare diphenyldifluoromethylphosphine oxide as follows: To a solution of diphenylphosphine oxide [25 grams (gm), 124 millimoles (mmol)] in tetrahydrofuran (THF) [600 milliliters (ml)] which has been cooled to −50° Celsius (° C.), add 70 ml of a solution of 1.8 molar (M) n-butyl lithium in hexane and allow to stand at −50° C. for 20 minutes (min). Add an excess of difluorochloromethane slowly and stir at −50° C. for 3 hours. Allow the mixture to come to room temperature and evaporate the solvent in vacuo. Redissolve the residue in chloroform/water (1/1, v/v; 200 ml). Separate the organic layer, dry with anhydrous magnesium sulfate, and evaporate to dryness. Purify by flash chromatography on silica gel eluting with toluene/ethyl acetate (1/1, v/v). Recrystallize from hexane/dichloromethane to yield the purified diphenyldifluoromethylphosphine oxide (melting point 93–94° C.).

Cool diisopropylamine [1.7 ml, 12 mmol] in THF (24 ml) to −20° C. in a chloroform/dry ice bath. Add n-butyl lithium [8.88 ml of a 1.35 molar (M) solution in hexane] in a dropwise manner and stir the mixture for 20 min. Cool the mixture to −70° C. in an acetone/dry ice bath. Add diphenyldifluoromethylphosphine oxide [3.02 gm, 12 mmol] in THF (12 ml) in a dropwise manner at such a rate that the temperature of the mixture does not rise above −65° C. Stir the mixture for 30 min and then add 4-ethoxy- 1-[(3,5-O-tetraisopropyldisiloxan-1,3-diyl)-2-keto-$\beta$-D-erythro-pentofuranosyl]-2(1H)-pyrimidone (5.12 gm, 10 mmol) in THF (20 ml) in a dropwise manner. Stir the mixture for 1 hour at −70° C., gradually warm the mixture to room temperature and then reflux for ½ hour. Cool the mixture to room temperature, add ethyl acetate (500 ml) and wash the organic mixture with saturated aqueous sodium bicarbonate (100 ml). Separate the organic layer, dry with anhydrous magnesium sulfate, and evaporate to dryness invacuo. Chromatograph the residue on a silica gel flash column eluting with ethyl acetate/hexane (1/1, v/v) to yield the title compound.

Step b: 2'-Deoxy-2'-difluoromethylidenecytidine

To a solution of 1.0 M tetrabutylammonium fluoride in THF (2.2 ml, 2.2 mmol) add 4-ethoxy-1-[(3,5-O-tetraisopropyldisiloxan-1,3-diyl)-$\beta$-D-erythro-pentofuran-2-(difluoromethylidene)osyl]-2(1H)-pyrimidone (546 mg, 1 mmol) and stir the mixture at room temperature for 2 hours. Neutralize the mixture with acetic acid, add flash silica gel to the mixture and evaporate to dryness in vacuo. Apply the residue to a flash silica gel column and elute with chloroform/ethanol (9/1, v/v) to provide 4-ethoxy-1-[$\beta$-D-erythro-pentofuran-2-(difluoromethylidene)osyl]-2(1H)-pyrimidone.

Heat a solution of 4-ethoxy-1-[$\beta$-D-erythro-pentofuran-2-(difluoromethylidene)osyl]-2(1H)-pyrimidone (909 mg, 3 mmol) in methanolic ammonia (10 ml, saturated at 0° C.) in a sealed tube at 100° C. for 2 days. Evaporate the solution to dryness to provide the title compound.

The following compounds can be made by procedures; analogous to those described above in Example 1:

2'-deoxy-2'-difluoromethylidene-5-methylcytidine
2'-deoxy-2'-difluoromethylidene-5-hydroxymethylcytidine
2'-deoxy-2'-dichloromethylidenecytidine
2'-deoxy-2'-difluoromethylidene-4'-thiocytidine
(±)-(1$\beta$,3$\alpha$,4$\beta$)-1-(4-amino-2-hydroxypyrimidin-6-yl)-2-difluoromethylidene-3-hydroxy-4-hydroxymethylcyclopentane.

EXAMPLE 2

2'-DEOXY-2'-DIFLUOROMETHYLIDENEURIDINE

Step a: 4-Ethoxy-1,[(3,5-O-tetraisopropyldisiloxan-1,3-diyl)-$\beta$-D-erythro-pentofuran-2-(difluoromethylidene)osyl]-2(1H)-pyrimidone Prepare the title compound as described in Example 1, step a.

Step b: 2'-Deoxy-2'-difluoromethylideneuridine

Prepare 4-ethoxy-1-[$\beta$-D-erythro-pentofuran-2-(difluoromethylidene)osyl]-2(1H)-pyrimidone as described in Example 1, step b.

Stir a solution of 4-ethoxy-1-[$\beta$-D-erythro-pentofuran-2-(difluoromethylidene)osyl]-2(1H)-pyrimidone (608 mg, 2 mmol) in THF (15 ml) and 1N sodium hydroxide (5 ml) at room temperature for 23 hours and then at 60° C. for 2 hours. Neutralize the reaction solution with Amberlite IRC-50 (H+-form) and filter off the resin. Evaporate the filtrate to dryness to provide the title compound.

The following compounds can be made by procedures analogous to those described above in Example 2:

2'-deoxy-2'-difluoromethylidenethymidine
2'-deoxy-2'-difluoromethylidene-5-hydroxymethyluridine
2'-deoxy-2'-dichloromethylideneuridine
2'-deoxy-2'-difluoromethylidene-4'-thiouridine
(±)-(1$\beta$,3$\alpha$,4$\beta$)-1-(2,4-dihydroxypyrimidin-6-yl)-2-difluoromethylidene-3-hydroxy-4-hydroxymethylcyclopentane

EXAMPLE 3

2'-DEOXY-2'-DIFLUOROMETHYLIDENEGUANOSINE

Step a: 1-[(3,5-O-tetraisopropyldisiloxan-1,3-diyl)-$\beta$-D-erythro-pentofuran-2-(difluoromethylidene)osyl]-guanine Prepare the title compound as described in Example 1, step a, from 1-[(3,5-O-tetraisopropyldisiloxan-1,3-diyl)-2-keto-$\beta$-D-erythro-pentofuranosyl]guanine (5.16 gm, 10 mmol).

Step b: 2'-Deoxy-2'-difluoromethylideneguanosine

Prepare the title compound as described in Example 1, step b, from 9-[(3,5-O-tetraisopropyldisiloxan-1,3-diyl)-$\beta$-D-erythro-pentofuran-2-(difluoromethylidene)osyl]guanine (0.55 gm, 1 mmol).

The following compounds can be made by procedures analogous to those described above in Example 3:

2'-deoxy-2'-dichloromethylideneguanosine
2'-deoxy-2'-difluoromethylidene-4'-thioguanosine A general synthetic procedure for the preparation of compounds of formula (1) wherein one of $X_1$ and $X_2$ is hydrogen is set forth in Scheme B.

SCHEME B

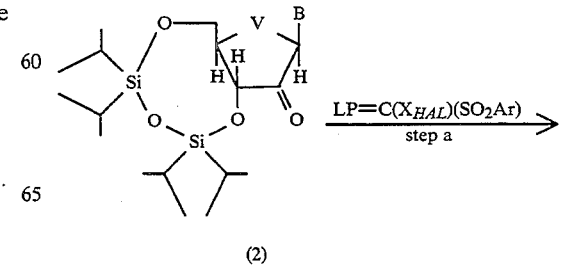

(2)

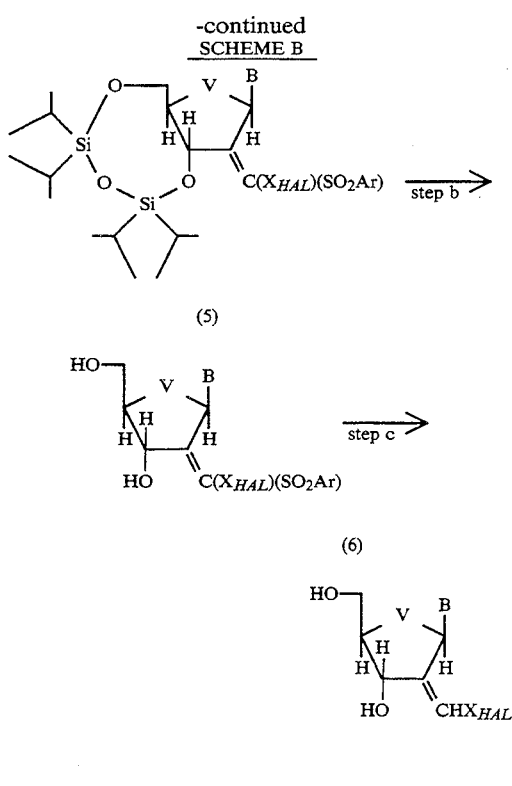

In step a, the ketone derivative (2), for example, 4-ethoxy-1-[(3,5-O-tetraisopropyldisiloxan-1,3-diyl)-β-D-erythropentofuran-2-keto-osyl]-2(1H)-pyrimidone, is reacted in a Wittig reaction with a phosphorus ylide as generally described for Scheme A. When a compound of formula (1) is desired wherein one of $X_1$ and $X_2$ is hydrogen, (2) can be reacted with an arylsulfonylhalomethylidene phosphorus ylide, to yield the corresponding 2-arylsulfonylhalomethylidene derivative (5) such as the 2-phenylsulfonylhalomethylidene derivative.

The appropriate arylsulfonylhalomethylidene phosphorus ylide can be prepared according to procedures which are well known and appreciated in the art of chemistry. For example, where a compound of formula (1) is desired wherein one of $X_1$ and $X_2$ is hydrogen, the appropriate ketone (2) can be reacted with an arylsulfonylhalomethylidene phosphorus ylide prepared by reacting a halo phosphate (such as diethylchloro phosphate) with a halomethylarylsulfone in the presence of a base (such as lithium diisopropylamide or lithium hexamethyldisilazane).

More specifically, when a compound of formula (1) is desired wherein one of $X_1$ and $X_2$ is fluorine and the other is hydrogen, the appropriate ketone (2) can be reacted with an arylsulfonylfluoromethylidene phosphorus ylide prepared by reacting a halo phosphate (such as diethylchloro phosphate) with fluoromethylarylsulfone in the presence of a base (such as lithium diisopropylamide).

In step b, the tetraisopropyldisiloxan blocking group of (5) is removed as described for Scheme A (step b), to yield the corresponding de-blocked 2-arylsulfonylhalomethylidene-substituted derivative (6). For example, a fluoride salt such as cesium fluoride or tetrabutylammonium fluoride can be used to remove the tetraisopropyldisiloxan blocking group.

In step c, the arylsulfonyl moiety of (6) is removed and replaced by a hydrogen atom to provide the corresponding 2-halomethylidene derivative (7). This can be accomplished according to procedures well known and appreciated in the art of chemistry, such as reacting (6) with an aluminum/mercury amalgam or a sodium/mercury amalgam or tributyltinhydride/azobisisobutylnitrile (AIBN) in refluxing benzene followed by an aqueous acid treatment.

The 2-arylsulfonylhalomethylidene-substituted derivative (6) is a novel compound useful as a chemical intermediate in the synthesis of compounds of formula (1) wherein one of $X_1$ or $X_2$ is hydrogen. The designation "Ar" in the compounds of formula (6) refers to a $C_6$-$C_{12}$ aryl group as defined hereinabove. The preferred compounds of formula (6) are those wherein Ar is phenyl.

Where a 4-alkoxy-substituted pyrimidone, such as the 4-ethoxy-substituted pyrimidone, is utilized as the starting material (2) for step a, the 4-alkoxy moiety of the pyrimidone base can be converted, in step c, to the 4-keto moiety to yield the corresponding uridine or thymidine derivative (7) or it can be converted to the 4-amino moiety to yield the corresponding cytidine derivative (7). These reactions can be effected according to procedures well known and appreciated in the art of chemistry as described for Scheme A.

As is readily apparent to one skilled in the art, the 2'-halomethylidene derivative represented by the compound (7) in Scheme B, exists as two geometric isomers which can be referred to as the (Z) and the (E) isomers. These isomers can be separated by using conventional separation techniques well known and appreciated in the art. For example, the geometric isomers may be resolved by column chromatography using a Dowex 1-X2 (OH⁻ form) resin.

The following example presents a typical synthesis as described by Scheme B. This example is understood to be illustrative only and is not intended to limit the scope of the present invention in any way.

EXAMPLE 4

(Z)- and (E-2'-DEOXY-2'-FLUOROMETHYLIDENECYTIDINE

Step a: 4-Ethoxy-1-[(3,5-O-tetraisopropyldisiloxan-1,3-diyl)-β-D-erythro-pentofuran-2-(2-fluoro-2-phenylsulfonyl methylidene)osyl]-2(1H)-pyrimidone Prepare diethylfluoromethylphenylsulfonylphosphonate as follows: To a solution of fluoromethylphenyl sulfone (500 mg, 2.87 mmol) in dry THF (30 ml) which has been cooled to about −60° C. in a dry 3-necked 100 ml flask with stirring bar, argon inlet valve, thermometer and rubber septum, add diethyl chlorophosphate (500 mg, 0.42 ml, 2.87 mmol) via syringe. To this mixture, add a solution of 1.65 M lithium diisopropylamide in cyclohexane (3.48 ml, 5.74 mmol) via syringe and follow the formation of diethylfluoromethylphenylsulfonylphosphonate by gas-liquid chromatography (GLC).

To the diethylfluoromethylphenylsulfonylphosphonate solution above add a solution of 4-ethoxy-1-[(3,5-O-tetraisopropyldisiloxan-1,3-diyl)-2-keto-β-D-erythropentofuranosyl]-2(1H)-pyrimidone (732 mg, 2 mmol) in dry THF (about 5 ml) and allow the reaction mixture to warm to room temperature overnight under an argon atmosphere. Pour the mixture into a saturated, ice-cold solution of ammonium chloride and extract the mixture with ethyl acetate (3 times, 75 ml each time). Combine the organic layers, dry with anhydrous magnesium sulfate, and evaporate to dryness. Chromatograph the residue on a silica gel flash column eluting with ethyl acetate/hexane (1/1, v/v) to provide the title compound.

Step b: 4-Ethoxy-1-[β-D-erythro-pentofuran-2-(2-fluoro-2-phenylsulfonylmethylidene)osyl]-2(1H)-pyrimidone To a solution of 1.0 M tetrabutylammonium fluoride in THF (2.2 ml, 2.2 mmol) add 4-ethoxy-1-[(3,5-O-tetraisopropyl-disiloxane-1,3-diyl)-β-D-erythro-pentofuran-2-(2-fluoro-2-phenylsulfonylmethylidene)osyl]-2(1H)-pyrimidone (668 mg, 1 mmol) and stir the mixture at room temperature for 2 hours. Neutralize the mixture with acetic acid, add flash silica gel to the mixture and evaporate to dryness in vacuo. Apply the residue to a flash silica gel column and elute with chloroform/ethanol (20/1, v/v) to provide the title compound.

Step c: (Z)- and (E)-2'-Deoxy-2'-fluoromethylidenecytidine

To a solution of 4-ethoxy-1-[B-D-erythro-pentofuran-2-(2-fluoro-2-phenylsulfonylmethylidene)osyl]-2(1H)-pyrimidone (854 mg, 2 mmol) in 10% aqueous THF (100 ml) under a nitrogen atmosphere, add aluminum amalgam (made from 0.04 gm aluminum in 2% aqueous $HgCl_2$). Stir and vent the mixture while refluxing for 2 hours. Filter the mixture and evaporate most of the THF in vacuo. Extract the residue with ethyl acetate (3 times, 25 ml each time), combine the organic layers and dry with anhydrous $Na_2SO_4$. Evaporate to dryness in vacuo and apply the residue to a flash silica gel column and elute with chloroform/ethanol (9/1, v/v) to provide (Z)- and (E)-4-ethoxy-1-[β-D-erythropentofuran-2-(2-fluoromethylidene)osyl]-2(1H)-pyrimidone as a mixture of geometric isomers.

Heat a solution of (Z)- and (E)-4-ethoxy-1-[β-D-erythropentofuran-2-(2-fluoromethylidene)osyl]-2(1H)-pyrimidone (858 mg, 3 mmol) in methanolic ammonia (10 ml, saturated at 0° C.) in a sealed tube at 100° C. for 2 days. Evaporate the solution to dryness and separate the (Z) and (E) isomers of the title compound by chromatography by applying the residue to a column packed with Dowex 1-X2 (OH⁻ form) and eluting with methanol.

The following compounds can be made by procedures analogous to those described above in Example 4:
- (E) and (Z)-2'-deoxy-2'-fluoromethylidene-5-methylcytidine
- (E) and (Z)-2'-deoxy-2'-fluoromethylidene-5-hydroxymethylcytidine
- (E) and (Z)-2'-deoxy-2'-chloromethylidenecytidine
- (E) and (Z)-2'-deoxy-2'-fluoromethylidene-4'-thiocytidine
- (±)-(1β,3α,4β)-1-(4-amino-2-hydroxypyrimidin-6-yl)-2(E and Z)-fluoromethylidene-3-hydroxy-4-hydroxymethylcyclopentane

EXAMPLE 5

(Z)- and (E)-2'-DEOXY-2'-FLUOROMETHYLIDENEURIDINE

Step a: 4-Ethoxy-1-[(3,5-O-tetraisopropyldisiloxan-1,3-diyl)-β-D-erythro-pentofuran-2-(2-fluoro-2-phenylsulfonyl methylidene)osyl]-2(1H)-pyrimidone Prepare the title compound as described in Example 4, step a.

Step b: 4-Ethoxy-1-[β-D-erythro-pentofuran-2-(2-fluoro)-2-phenylsulfonylmethylidene)osyl]-2(1H)-pyrimidone Prepare the title compound as described in Example 4, step b.

Step c: (Z)- and (E)-2'-Deoxy-2'-fluoromethylideneuridine

Prepare 4-ethoxy-1-[β-D-erythro-pentofuran-2-(2-fluoromethylidene)osyl]-2(1H) -pyrimidone as described in Example 4, step c.

Stir a solution of 4-ethoxy-1-[β-D-erythro-pentofuran-2-(2-fluoromethylidene)osyl]-2(1H)-pyrimidone (572 mg, 2 mmol) in THF (15 ml) and 1N sodium hydroxide (5 ml) at room temperature for 23 hours and then at 60° C. for 2 hours. Neutralize the reaction solution with Amberlite IRC-50 (H⁺-form) and filter off the resin. Evaporate the filtrate to dryness to provide the title compounds. Separate the (Z) and (E) isomers of the title compound by chromatography by applying the residue to a column packed with Dowex 1-X2 (OH⁻ form) and eluting with 0.1 M ammonium bicarbonate.

The following compounds can be made by procedures analogous to those described above in Example 5:
- (E) and (Z)-2'-deoxy-2'-fluoromethylidene-5-hydroxymethyl uridine
- (E) and (Z)-2'-deoxy-2'-fluoromethylidenethymidine
- (E) and (Z)-2'-deoxy-2'-chloromethylideneuridine
- (E) and (Z)-2'-deoxy-2'-fluoromethylidene-4'-thiouridine

EXAMPLE 6

(Z)- and (E)-2'-DEOXY-2'-FLUOROMETHYLIDENEGUANOSINE

Step a: 9-[(3,5-O-tetraisopropyldisiloxan-1,3-diyl)-β-D-erthyro-pentofuran-2-(2-fluoro-2-phenylsulfonyl methylidene)osyl]guanine Prepare the title compound from 9-[(3,5-O-tetraisopropyldisiloxan-1,3-diyl)-2-keto-β-D-erythropentofuranosyl]guanine (5.16 gm, 10 mmol) as described in Example 4, step a.

Step b: 9-[β-D-erythro-pentofuran-2-(2-fluoro-2-phenylsulfonylmethylidene)osyl]guanine Prepare the title compound from 9-[(3,5-O-tetraisopropyldisiloxan-1,3-diyl)-β-D-erythro-pentofuran-2-(2-fluoro-2-phenylsulfonylmethylidene)osyl]guanine as described in Example 4, step b.

Step c: (Z)- and (E)-2'-Deoxy-2'-fluoromethylidenequanosine

Prepare the title compound from 9-[β-D-erythro-pentofuran-2-(2-fluoro-2-phenylsulfonylmethylidene)osyl]guanine as described in Example 4, step c.

The following compounds can be made by procedures analogous to those described above in Example 6:
- (Z)- and (E)-2'-deoxy-2'-chloromethylideneguanosine
- (Z)- and (E)-2'-deoxy-2'-fluoromethylidene-4'-thioguanosine
- (±)-(1β,3α,4β)-1-(2-amino-6-hydroxy-9H-purin-9-yl)-2(E and Z)-fluoromethylidene-3-hydroxy-4-hydroxymethylcyclopentane A general synthetic procedure for the preparation of compounds of formula (Ia) is set forth in Scheme C.

This scheme is especially useful for compounds of formula (1a) wherein R is hydrogen.

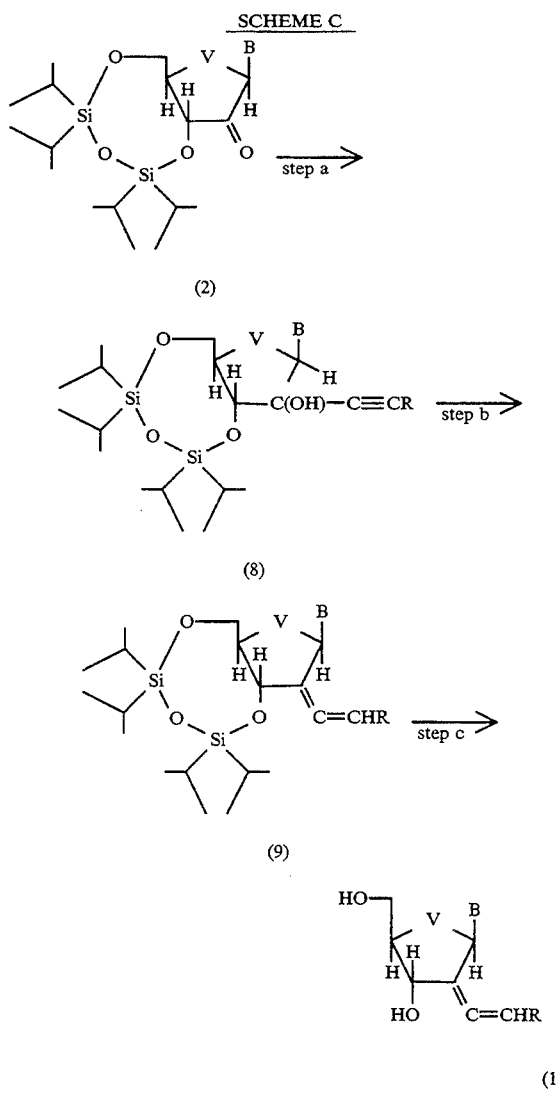

In step a, the ketone derivative (2), for example, 4-ethoxy-1-[(3,5-O-tetraisopropyldisiloxan-1,3-diyl)-β-D-erythropentofuran-2-keto-osyl]-2(1H)-pyrimidone, can be reacted with an acetylenic Grignard reagent such as that represented by the general formula RC≡CMgBr, to yield the corresponding 2-ethynyl alcohol (8). Alternatively, the alcohol (8) can be prepared from other organometallic compounds made from reactive metals, such as that represented by the general formula RC≡CLi.

The appropriate Grignard reagent, or other organometallic reagent, can be prepared according to methods and procedures which are well known and appreciated in the art of chemistry such as those described by J. March in "Advanced Organic Chemistry: Reactions, Mechanisms and Structure", McGraw-Hill Book Company, 684–88 and 697–98 (1968). For example, a Grignard reagent of acetylene or an alkyl-substituted acetylene can be prepared by treating acetylene or an alkyl-substituted acetylene with methylmagnesium bromide under anhydrous conditions.

It is of course well appreciated by one skilled in the art that the 2-ethynyl alcohol (8) can exist as one of two diasteriomeric isomers, i.e., one wherein the ethynyl group is on the same side of the furanosyl ring as the 3-hydroxy group and one wherein the ethynyl group is on the same side of the furanosyl ring as the purine or pyrimidine group. Where 4-ethoxy-1-[(3,5-O-tetraisopropyldisiloxan-1,3-diyl)-β-D-erythropentofuran-2-keto-osyl]-2(1H)-pyrimidone is utilized as the starting material (2), these diasteriomeric isomers are named 4-ethoxy-1-[(3,5-O-tetraisopropyldisiloxan-1,3-diyl)-β-D-ribopentofuran-2-(ethynyl)osyl]-2(1H)-pyrimidone and 4-ethoxy-1-[(3,5-O-tetraisopropyldisiloxan-1,3-diyl)-β-D-arabino-pentofuran-2-(ethynyl)osyl]-2(1H)-pyrimidone.

In step b, the 2-ethynyl alcohol (8) is reduced to yield the 2-ethenylidene derivative (9). This reduction can be carried out according to methods and procedures which are well known and appreciated in the art of chemistry such as by treating the 2-ethynyl alcohol (8) with lithium aluminum hydride and aluminum chloride.

In step c, the tetraisopropyldisiloxan blocking group of (9) is removed as described for Scheme A (step b), to yield the corresponding de-blocked 2-ethenylidene derivative (1a).

Where a 4-alkoxy-substituted pyrimidone, such as 4-ethoxy-substituted pyrimidone, is utilized as the starting material (2) for step a, the 4-alkoxy moiety of the pyrimidone base can be converted to the 4-keto moiety to yield the corresponding uridine or thymidine derivative (1a) or it can be converted to the 4-amino moiety to yield the corresponding cytidine derivative (1a). These reactions can be effected according to procedures well known and appreciated in the art of chemistry as described for Scheme A.

The following example presents a typical synthesis as described by Scheme C. This example is understood to be illustrative only and is not intended to limit the scope of the present invention in any way.

EXAMPLE 7

2'-DEOXY-2'-ETHENYLIDENECYTIDINE

Step a: 4-Ethoxy-1-[(3,5-O-tetraisopropyldisiloxan-1,3-diyl)-β-D-(ribo- or arabino-)pentofuran-2-(ethynyl-)osyl]-2(1H)-pyrimidone At 0° C., saturate THF (750 ml) with acetylene and add 1.95N methylmagnesium bromide (51 ml, 0.1 mol) in a dropwise manner while acetylene is still bubbling through the solution. Stop the acetylene stream 20 min after the addition of the methyl magnesium bromide is complete and purge for 20 min with argon. To this solution add 4-ethoxy-1-[(3,5-O-tetraisopropyldisiloxan-1,3-diyl)-β-D-erythro-pentofuran-2-keto-osyl]-2(1H)-pyrimidone (2.73 gm, 5 mmol) in THF (20 ml), warm the reaction mixture to room temperature and stir for 16 hours. Add 1600 ml of ethyl acetate and wash the mixture with saturated aqueous NH4Cl (200 ml). Dry the organic layer with anhydrous magnesium sulfate and evaporate to dryness in vacuo. Chromatograph the residue on a silica gel flash column eluting with ethyl acetate/hexane (1/1, v/v) to provide the title compound.

Step b: 4-ethoxy-1-[(3,5-O-tetraisopropyldisiloxan-1,3-diyl)-β-D-erythro-pentofuran-2-(ethenylidene)osyl]-2(1H)-pyrimidone To a stirred solution of lithium aluminum hydride (76 mg, 2 mmol) and aluminum chloride (132 mg, 1 mmol) in anhydrous diethyl ether (4 ml) which has been cooled to 0° C., add a solution of 4-ethoxy-1-[(3,5-O-tetraisopropyldisiloxan-1,3-diyl)-β-D-(ribo- or arabino-)pentofuran-2-(ethynyl)osyl]-2(1H)-pyrimidone (531 mg, 1 mmol) in anhydrous diethyl ether (2 ml) in a dropwise manner. Stir the reaction mixture for 1 hour and then quench the reaction by adding 10% potassium hydrogen sulfate (10 ml). Wash the aqueous solution with ethyl acetate (3 times, 20 ml each time). Combine the organic layers, dry with anhydrous magnesium sulfate, and concentrate the solution in vacuo. Chromatograph the residue on a silica gel flash column eluting with ethyl acetate/hexane (1/1, v/v) to provide the title compound.

Step c: 2'-Deoxy-2'-ethenylidenecytidine

To a solution of 1.0 M tetrabutylammonium fluoride in THF (2.2 ml, 2.2 mmol) add 4-ethoxy-1-[(3,5-O-tetraisopropyldisiloxan-1,3-diyl)-β-D-erythro-pentofuran-2(erthyro-pentofuran-2-(ethenylidene)osyl]-2(1H)-pyrimidone (513 mg, 1 mmol) and stir the mixture at room temperature for 2 hours. Neutralize the mixture with acetic acid, add flash silica gel to the mixture and evaporate to dryness in vacuo. Apply the residue to a flash silica gel column and elute with chloroform/ethanol (20/1, v/v) to provide 4-ethoxy-1-[β-D-erythro-pentofuran-2-(ethenylidene)osyl]-2(1H)-pyrimidone.

Heat a solution of 4-ethoxy-1-[β-D-erythro-pentofuran-2-(ethenylidene)osyl]-2(1H)-pyrimidone (840 mg, 3 mmol) in methanolic ammonia (10 ml, saturated at 0° C.) in a sealed tube at 100° C. for 2 days. Evaporate the solution to dryness to provide the title compound.

The following compounds can be made by procedures analogous to those described above in Example 3:
2'-deoxy-2'-ethenylidene-5-methylcytidine
2'-deoxy-2'-ethenylidene-5-hydroxymethylcytidine
2'-deoxy-2'-ethenylidene-4'-thiocytidine
(±)-(1β,3α,4β)-1-(4-amino-2-hydroxypyrimidin-6-yl)-2-ethenylidene-3-hydroxy-4-hydroxymethylcyclopentane

EXAMPLE 8
2'-DEOXY-2'-ETHENYLIDENEURIDINE

Step a: 4-Ethoxy-1-[(3,5-O-tetraisopropyldisiloxan-1,3-diyl)-β-D-(ribo- or arabino-)pentofuran-2-(ethynyl)osyl]-12(1H)pyrimidone Prepare the title compound as described in Example 7, step a.

Step b: 4-Ethoxy-1-[3,5-O-tetraisopropyldisiloxan-1,3-diyl)-β-D-erythro-pentofuran-2-ethenylidene)osyl]-2(1H)-primidone Prepare the title compound as described in Example 7, step b.

Step c: 2'-Deoxy-2'-ethenylideneuridine

Prepare 4-ethoxy-1-[β-D-erythro-pentofuran-2-(ethenylidene)osyl]-2(1H)-pyrimidone as described in Example 7, step c.

Stir a solution of 4-ethoxy-1-[β-D-erythro-pentofuran-2-ethenylidene)osyl]-2(1H)-pyrimidone (560 mg, 2 mmol) in THF (15 ml) and 1N sodium hydroxide (5 ml) at room temperature for 23 hours and then at 60° C. for 2 hours. Neutralize the reaction solution with Amberlite IRC-50 (H+-form) and filter off the resin. Evaporate the filtrate to dryness to provide the title compound.

The following compounds can be made by procedures analogous to those described above in Example 8:
2'-deoxy-2'-ethenylidene-5-hydroxymethyluridine
2'-deoxy-2'-ethenylidenethymidine
2'-deoxy-2'-ethenylidene-4'-thiouridine

EXAMPLE 9
2'-DEOXY-2'-ETHENYLIDENEGUANOSINE

Step a: 9-[(3,5-O-tetraisopropyldisiloxan-1,3-diyl)-β-D-(ribo- or arabino-)pentofuran-2-(ethynyl)osyl]guanine Prepare the title compound from 9-[(3,5-O-tetraisopropyldisiloxan-1,3-diyl)-2-keto-β-D-erythropentofuranosyl]guanine (2.58 gm, 5 mmol) as described in Example 7, step a.

Step b: 9-[(3,5-O-tetraisopropyldisiloxan-1,3-diyl)-β-D-erythro-pentofuran-2-(ethenylidene)osyl]guanine Prepare the title compound from 9-[(3,5-O-tetraisopropyldisiloxan-1,3-diyl)-β-D-(ribo- or arabino-) pentofuran-2-(ethynyl)osyl]guanine as described in Example 7, step b.

Step c: 2'-Deoxy-2'-ethenylideneguanosine

Prepare the title compound from 9-[(3,5-O-tetraisopropyldisiloxan-1,3-diyl)-β-D-erythro-pentofuran-2-(ethenylidene)osyl]guanine as described in Example 7, step c.

The following compounds can be made by procedures analogous to those described above in Example 9:
2'-deoxy-2'-ethenylidene-4'-thioguanosine A general synthetic procedure for the preparation compounds of formula (1b) is set forth in Scheme D.

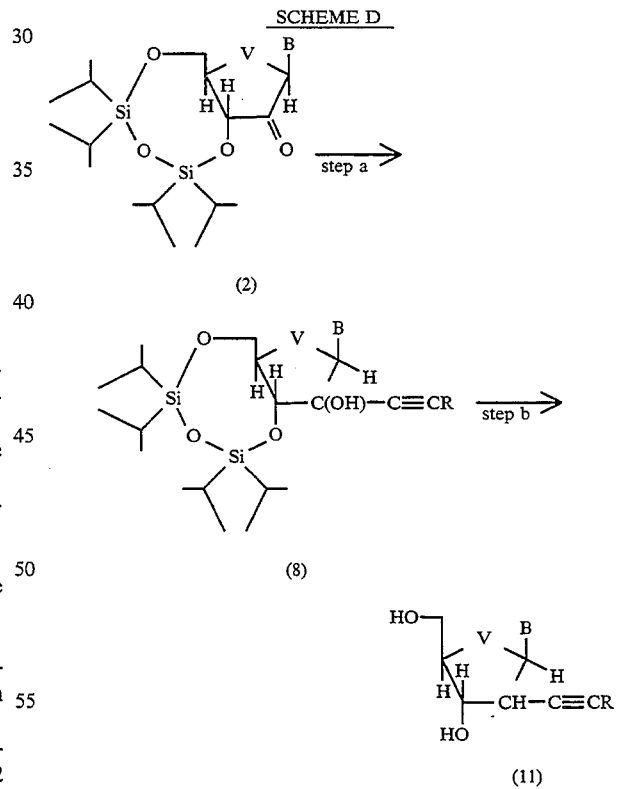

In step a, the ketone derivative (2), for example, 4-ethoxy-1-[(3,5-O-tetraisopropyldisiloxan-1,3-diyl)-β-D-erythro-pentofuran-2-keto-osyl]-2(1H)-pyrimidone, can be reacted as described in Scheme C (step a) to yield the corresponding 2-ethynyl alcohol (8). As described for Scheme C, the 2-ethynyl alcohol (8) can exist as two diasteriomeric isomers, for example, 4-ethoxy-1-[(3,5-O-tetraisopropyldisiloxan-1,3-diyl)-β-D-ribo-pentofuran-2-(ethynyl)osyl]-2(1H)-pyrimidone and 4-ethoxy-1-

[(3,5-O-tetraisopropyldisiloxan-1,3-diyl)-β-D-arabino-pentofuran-2-(ethynyl)osyl]-2(1H)-pyrimidone.

In step b, the 2-ethynyl alcohol (8) is reduced and the tetraisopropyldisiloxan blocking group is removed to yield the 2-ethynyl derivative (11). This reduction can be carried out according to methods and procedures which are well known and appreciated in the art of chemistry by treating the 2-ethynyl alcohol (8) with a reducing agent such as triethylsilane in the presence of an acid such as trifluoroacetic acid.

Where a 4-alkoxy-substituted pyrimidone, such as the 4-ethoxy-substituted pyrimidone, is utilized as the starting material (2) for step a, the 4-alkoxy moiety of the pyrimidone base can be converted to the 4-keto moiety to yield the corresponding uridine or thymidine derivative (11) or it can be converted to the 4-amino moiety to yield the corresponding cytidine derivative (11). These reactions can be effected according to procedures well known and appreciated in the art of chemistry as described for Scheme A.

Again it will be appreciated that the 2'-ethynyl derivative (11) can exist as one of two diasteriomeric isomers, i.e., one wherein the ethynyl group is on the same side of the furanosyl ring as the 3-hydroxy group and one wherein the ethynyl group is on the same side of the furanosyl ring as the purine or pyrimidine group. For example, where a cytidine derivative is desired, these geometric isomers can be named 2'-deoxy-2'(R)-ethynylcytidine (or 4-keto-1-[β-D-erythro-pentofuran-2(R)-(ethynyl)osyl]-2(1H)-pyrimidone) and 2'-deoxy-2'(S)-ethynylcytidine (or 4-keto-1-[β-D-erythro-pentofuran-2(S)-(ethynyl)osyl]-2(1H)-pyrimidone), respectively.

As is readily apparent to one skilled in the art, the (R) and the (S) diasteriomeric isomers of the 2'-ethynyl derivatives (11) can be separated using conventional separation methods. For example, the diasteriomeric isomers may be resolved by column chromatography using known methods and techniques.

The following example presents a typical synthesis as described by Scheme D. This example is understood to be illustrative only and is not intended to limit the scope of the present invention in any way.

EXAMPLE 10

2'-DEOXY-2'(R or S)-ETHYNYLCYTIDINE

Step a: 4-Ethoxy-1-[(3,5-O-tetraisopropryldisiloxan-1,3-diyl)-β-D-(ribo- or arabino-)pentofuran-2-(ethynyl)osyl]-2(1H)-pyrimidone Prepare the title compound as described in Example 7, step a.

Step b: 2'-Deoxy-2'(R and S)-ethynylcytidine

Dissolve 4-ethoxy-1-[(3,5-O-tetraisopropyldisiloxan-1,3-diyl)-β-D-(ribo- or arabino-)pentofuran-2-(ethynyl)osyl]-2(1H)-pyrimidone (490 mg, 0.94 mmol) in dichloromethane (3 ml) under a nitrogen atmosphere and cool the solution in an ice bath Add trifluoroacetic acid (0.54 ml, 7.08 mmol) followed by triethylsilane (0.27 ml, 1.71 mmol) and stir the solution overnight at room temperature. Dilute the reaction mixture with ethyl acetate (10 ml) and wash with ice cold 1N sodium hydroxide solution (2 times, 5 ml each time). Dry the organic layer with anhydrous magnesium sulfate and evaporate to dryness to yield 4-ethoxy-1-[β-D-erythro-pentofuran-2(R and S)(ethynyl)osyl]-2(1H)-pyrimidone.

Heat a solution of 4-ethoxy-1-[β-D-erythro-pentofuran-2(R and S)-(ethynyl)osyl]-2(1H)-pyrimidone (885 mg, 3 mmol) in methanolic ammonia (10 ml, saturated at 0° C.) in a sealed tube at 100° C. for 2 days. Evaporate the solution to dryness and separate the (R)- and (S)-isomers on a Dowex 1-X2 (OH$^-$ form) chromatographic column to provide the title compounds.

The following compounds can be made by procedures analogous to those described above in Example 10:

2'-deoxy-2'(R or S)-ethynyl-5-methylcytidine

2'-deoxy-2'(R or S)-ethynyl-5-hydroxymethylcytidine

2'-deoxy-2'(R or S)-ethynyl-4'-thiocytidine (±)-(1β,3α,4β)-1-(4-amino-2-hydroxypyrimidin-6-yl)-2-(α and β)-ethynyl-3-hydroxy-4-hydroxymethylcyclopentane

EXAMPLE 11

2'-DEOXY-2'(R and S)-ETHYNYLURIDINE

Step a: 4-Ethoxy-1-[(3,5-O-tetraisopropyldisiloxan-1,3-diyl)-β-D-(ribo- or arabino-)pentofuran-2-(ethynyl)osyl]-2(1H)-pyrimidone Prepare the title compound as described in Example 7, step a.

Step b: 2'-Deoxy-2'(R and S)-ethynyluridine

Prepare 4-ethoxy-1-[β-D-erythro-pentofuran-2(R and S)-(ethynyl)osyl]-2(1H)-pyrimidone as described in Example 10, step b.

Stir a solution of 4-ethoxy-1-[β-D-erythro-pentofuran-2(R and S)-(ethynyl)osyl]-2(1H)-pyrimidone(590 mg, 2 mmol) in THF (15 ml) and 1N sodium hydroxide (5 ml) at room temperature for 23 hours and then at 60° C. for 2 hours. Neutralize the reaction solution with Amberlite IRC-50 (H$^+$-form) and filter off the resin. Evaporate the filtrate to dryness and separate the (R)- and (S)- isomers on a Dowex 1-X2 (OH$^-$ form) chromatographic column to provide the title compounds.

The following compounds can be made by procedures analogous to those described above in Example 11:

2'-deoxy-2'(R and S)-ethynyl-5-hydroxymethyiuridine

2'-deoxy-2'(R and S)-ethynylthymidine

2'-deoxy-2'(R and S)-ethynyl-4'-thiouridine

EXAMPLE 12

2'-DEOXY-2'(R and S)-ETHYNYLGUANOSINE

Step a: 9-[(3,5-O-tetraisopropyldisiloxan-1,3-diyl)-β-D-(ribo- or arabino-)pentofuran-2-(ethynyl)osyl]guanine Prepare the title compound from 9-[(3,5-O-tetraisopropyldisiloxan-1,3-diyl)-2-keto-β-D-erythropentofuranosyl]guanine (2.58 gm, 5 mmol) as described in Example 7, step a.

Step b: 2'-Deoxy-2'(R and S)-ethynylguanosine

Prepare the title compounds from 9-[(3,5-O-tetraisopropyldisiloxan-1,3-diyl)-B-D-(ribo- or arabino-)pentofuran-2-(ethynyl)osyl]guanine as described in Example 10, step b.

The following compounds can be made by procedures analogous to those described above in Example 9:

2'-deoxy-2'(R and S)-ethynyl-4'-thioguanosine

2'-deoxy-2'(R and S)-8-azaguanosine

2'-deoxy-2'(R and S)-N$^3$-methylguanosine

2'-deoxy-2'(R and S)-8-chloroguanosine.

Scheme E provides an alternative and preferred synthetic procedure for the preparation of compounds of formula (1) wherein one of X$_1$ and X$_2$ is hydrogen.

SCHEME E

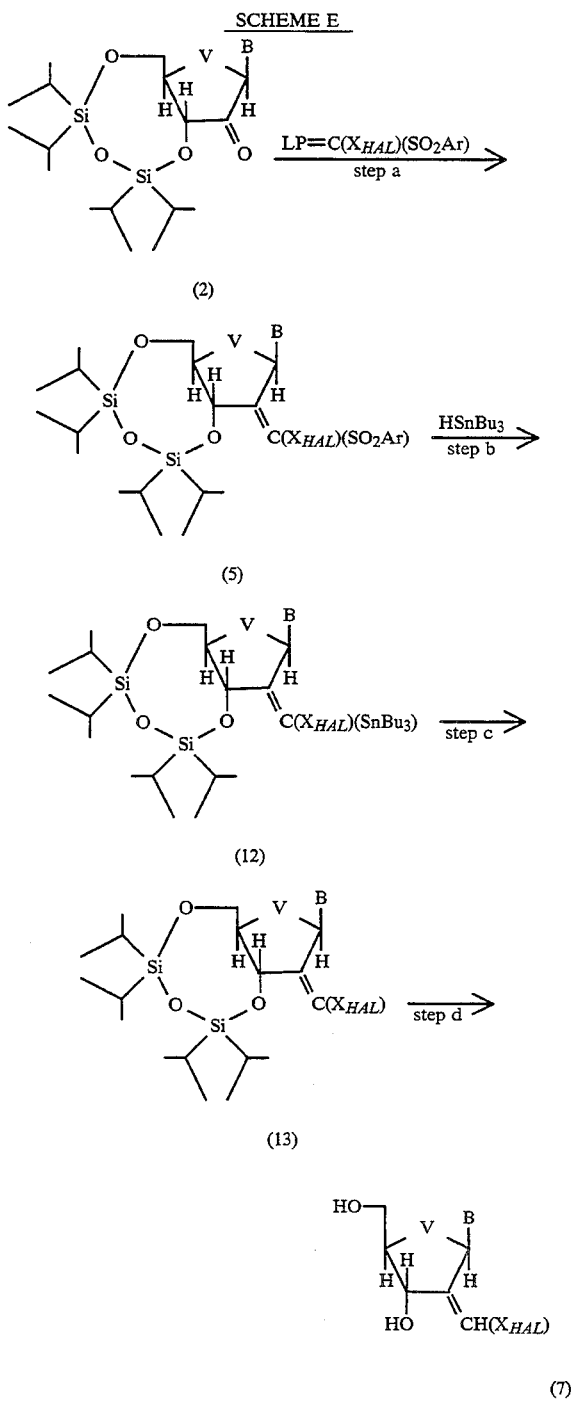

In step a, the ketone derivative (2), for example, 4-ethoxy-1-[(3,5-O-tetraisopropyldisiloxan-1,3-diyl)-β-D-erythropentofuran-2-keto-osyl]-2(1H)-pyrimidone, is reacted in a Wittig reaction with a phosphorus ylide as generally described for Schemes A and B.

In step b, the 2-arylsulfonylhalomethylidene derivative (5) is converted to the corresponding 2-tributyl-tin-halomethylidene derivative (12). For example, this reaction can be accomplished by reacting (5) with tributyl-tin hydride (HSnBu₃) in the presence of 2,2'-azobisisobutyronitrile (AIBN) in a suitable solvent such as benzene. The geometric isomers of the 2-tributyl-tin-halomethylidene derivative (12) can optionally be isolated using procedures and techniques which are well known and appreciated in the art. For example, the geometric isomers of (12) can be separated conveniently by flash chromatography (silica gel) eluting with 7% ethyl acetate in hexane.

In step c, the tributyl-tin moiety of (12) is removed and replaced by a hydrogen atom to provide the corresponding 2-halomethylidene derivative (13). This can be accomplished by procedures as are well known and appreciated in the art such as by reacting (12) with dilute acetic acid, ammonia in methanol or sodium methoxide.

In step d, the tetraisopropyldisiloxan blocking group of (13) is removed as described for Scheme A (step b), to yield the corresponding de-blocked 2'-halomethylidene derivative (7). For example, a fluoride salt such as cesium fluoride or tetrabutylammonium fluoride can be used to remove the tetraisopropyldisiloxan blocking group.

Where a 4-alkoxy-substituted pyrimidone, such as the 4-ethoxy-substituted pyrimidone, is utilized as the starting material (2) for step a, the 4-alkoxy moiety of the pyrimidone base can be converted to the 4-keto moiety to yield the corresponding uridine or thymidine derivative (7) or it can be converted to the 4-amino moiety to yield the corresponding cytidine derivative (7). These reactions can be effected according to procedures well known and appreciated in the art of chemistry as described for Scheme A.

As is readily apparent to one skilled in the art, the 2'-halomethylidene derivative represented by the compound (7) in Scheme E, exists as two geometric isomers which can be referred to as the (Z) and the (E) isomers. These isomers can be separated by using conventional separation techniques well known and appreciated in the art. For example, the geometric isomers may be resolved by column chromatography using a Dowex 1-X2 (OH⁻ form) resin. Optionally, the 2-tributyl-tin-halomethylidene derivative (12) or the corresponding 2-halomethylidene derivative (13) can conveniently be resolved into its geometric isomers using known techniques.

The following example presents a typical synthesis as described by Scheme E. This example is understood to be illustrative only and is not intended to limit the scope of the present invention in any way.

EXAMPLE 13

(E)-2'-DEOXY-2'-FLUOROMETHYLIDENECYTIDINE

2',3',5'-Tri-O-acetyluridine: In a 2L 3-neck flask equipped with a mechanical stirrer was placed uridine (100 g, 0.41 mol), acetic anhydride (155 mL, 1.64 mol), 4-dimethylaminopyridine (300 mg, 2.5 mmol) and acetonitrile (800 mL). Triethylamine (228 mL, 1.64 mol) was added slowly via a dropping funnel. The reaction exothermed (24° C. to 36° C.) slowly. After all of the triethylamine was added, the reaction was stirred at room temperature for 1 hour and was quenched with methanol (700 mL). After 18 hours, the reaction was concentrated and the residue partitioned between CHCl₃ (2×400 mL) and water (800 mL). The organic solution was dried over MgSO₄ and concentrated to give 200 g of a light tan viscous oil which slowly crystallized. Recrystallization (isopropanol/1.3 L) gave 137 g (93%) of the title compound as white crystals, mp 129–130° C.

¹H NMR (CDCl₃): δ2.11(s,3); 2.14(s,3); 2.15(s,3); 4.36(s,3);
5.33–5.36(m,2); 5.80(d,1,J=8.1Hz); 6.03–6.07(m,1); 7.40(d,1,J=8.2Hz); 9.25(br s,1).
MS (CI/CH₄) m/z 371 (MH+).
Analytical:
Calculated for C₁₅H₁₈N₂O₉: C, 48.65; H, 4.90; N, 7.56

Found: C, 48.56; H, 4.88; N, 7.50

4-Ethoxy-1-(β-D-ribofuranosyl)2(1H)-pyrimidinone

In a 1 L flask was placed 2′,3′,5′-tri-O-acetyluridine (60 g, 0.162 mol), thionyl chloride (150 mL, 2.07 mol), CHCl₃ (1 L passed through basic alumina) and DMF (5 mL). The reaction was refluxed gently for 6.5 hours. After cooling to room temperature, the reaction was concentrated and any remaining thionyl chloride azeotroped using dry toluene (2x). In a flask equipped with a mechanical stirrer, the residue was dissolved in ethanol (500 mL), cooled to 0° C. and freshly prepared 1M sodium ethoxide (500 mL) was added dropwise. The reaction was stirred for 2 hours at room temperature and then refluxed for 2 hours. The cooled reaction was filtered and concentrated, The brown residue was dissolved in CHCl₃ (about 100 mL) and purified by flash chromatography on silica gel (1.3 Kg) using 8% ethanol/CHCl₃ (3 L) then 16% ethanol/CHCl₃. The fractions containing the desired product were concentrated and dried to give 30.9 g (70.1%) of the title compound as a tan solid, mp 110–114° C.

¹H NMR (DMSO-d₆): δ1.25(t,3); 3.70(m,2); 3.90(m,3); 4.27(q,2);
5.05(d,1,J=5.5Hz);  5.14(t,1,J=5.1Hz); 5.44(d,1,J=5.1Hz);
5.78(d,1,J=3.2Hz);  6.00(d,1,J=7.5Hz); 8.30(d,1,J=7.5Hz).
MS (CI/CH₄) m/z 273 ( MH+ ).

4-Ethoxy-1-(3,5-O-tetraisopropyldisiloxan-1,3-diyl-β-D-ribofuranosyl)-2(1H)-pyrimidone Under argon, a solution of 4-ethoxy-1-(β-D-ribofuranosyl)-2(1H)-pyrimidinone (60 g, 0.22 mol), imidazole (30 g, 0.44 mol), 4-dimethylaminopyridine (91 g, 8 mmol) and DMF (50 mL) was cooled to about 5° C. and a solution of 1,3-dichloro-1,1,3,3-tetraisopropyl-disiloxane (69.4 g, 0.22 mol) in DMF (50 mL) was added dropwise. After 2 hours, the reaction was allowed to warm to room temperature and was stirred for 18 hours. The reaction was concentrated then partitioned between water and ethylacetate. After a second ethyl acetate extraction, the combined organic solutions were dried and concentrated to provide the crude title compound (97 g; 86%) as a viscous brown oil.

¹H NMR (CDCl₃) (purified sample):
δ0.95–1.15(m,28); 1.38(y,3);
3.17(1,d); 4.00–4.30(m,5); 4.45(2,q); 5.78(s,1); 5.85(d,1,J=7Hz); 7.98(d,1,J=7Hz).
MS (CI/CH₄) m/z 515 (MH+).

4-Ethoxy-1-(3,5-O-tetraisopropyldisiloxan-1,3-diyl-β-D-erythro-pentofuran-2-ulosyl)-2(1H)-pyrimidinone:
Under argon, oxalyl chloride (446 mg, 3.51 mmol) in CH₂Cl₂ (20 mL) was cooled to −70° C. and DMSO (593 mg, 7.6 mmol) was added slowly via syringe. After 15 minutes, a solution of 4-ethoxy-1-(3,5-O-tetraisopropyldisiloxan-1,3-diyl-β-D-ribofuranosyl)-2(1H)-pyrimidone (1.4 g, 2.7 mmol) in CH₂Cl₂ (10 mL) was added via syringe. After 2 hours at −70° C., triethylamine (1.64 g, 16.2 mmol) was added and the reaction was held at −70° C. for another hour. The reaction was then allowed to warm to room temperature and was quenched with water (10 mL). The CH₂Cl₂ layer was washed a second time with water, dried over MgSO₄ and concentrated. Flash chromatography (75 g silica gel/20% ethylacetate in hexane) gave 1.09 g (78%) of the title compound as a white foam (hydroscopic).

¹H NMR (CDCl₃): β0.98–1.18(m,28); 1.36(t,3); 3.95–4.15(m,3);
4.42(q,2); 4.95(m,1); 5.11(s,1); 5.92(d,1,J=7.7Hz); 7.40(d,1,J=7.4Hz).
MS (CI/CH₄) m/z 513 (MH+).

(Z)-1-[2-Deoxy-2-[fluoro(phenylsulfonyl)methylene]-3,5-O-[1,1,3,3-tetrakis(1-methylethyl)-1,3-disiloxanediyl]-β-D-erythro-pentofuranosyl]-4-ethoxy-2(1H),pyrimidinone and (E)-1)-[2-Deoxy-2-[fluoro(-phenylsulfonyl)methylene[-3,5-O-[1,1,3,3-tetrakis(1-methylethyl)-1,3-disiloxanediyl]-β-D-erythro-pentofuranosyl]-4-ethoxy-2(1H)-pyrimidinone Under argon, methyl phenyl sulfoxide (22.5 g, 160 mmol), CHCl₃ (100 mL), diethylaminosulfur trifluoride (DAST) (44.2 g, 275 mmol) and SbCl₃ (about 200 mg) were stirred in a 1 L flask equipped with a large air condenser. The reaction was cooled with a water bath and after 5 hours, a mild exotherm was observed [Note: DAST is very corrosive and should be handled using appropriate safety equipment. This reaction has a latent exotherm and should be cooled with a room temperature water bath.] After stirring an additional hour, the reaction mixture was poured onto 1 L ice cold saturated NaHCO₃ containing 10 g NaOH (foams). The aqueous layer was extracted with CHCl₃ (3×100 mL). The extracts were combined, washed with saturated NaHCO₃ (2×200 mL) and dried (K₂CO₃). To the filtered CHCl₃ solution was added portionwise solid 3-chloroperbenzoic acid (90 g, 350 mmol assuming 75% purity). The temperature was held below 45° C. The reaction mixture was washed consecutively with aqueous sodium metabisulfite, saturated NaHCO₃ (500 mL) containing NaOH (10 g), and saturated aqueous NaHCO₃. The CHCl₃ layer was dried (MgSO₄), filtered and concentrated to a colorless reflux. The mixture was stirred vigorously and seeded as it cooled to room temperature. White crystals where collected and dried to yield 26.4 g (94%) of fluoromethyl phenyl sulfone, mp 53.4–54.5° C.

¹H NMR (CDCl₃): δ5.14(d,2,J=47.5 Hz); 7.59–7.99(m,5).
¹⁹F NMR (CDCl₃): δ−211.24 (t,J=47.4Hz ).
MS (EI) m/z 175 (M+·).
Analytical:
Calculated for C₇H₇FO₂S: C, 48.26; H, 4.05.
Found: C, 47.99; H, 4.00

Under argon, a solution of fluoromethylphenylsulfone (4.1 g, 23.5 mmol) in THF (200 mL) was cooled to −78° C. Diethyl chlorophosphate (freshly distilled, 3.4 mL, 23.5 mmol) was added via syringe followed by slow addition of a lithium hexamethyldisilazane solution (1M, 46 mL, 46 mmol). After 15 minutes, the reaction mixture was allowed to warm to 0° C. and a solution of oven dried 4-ethoxy-1-(3,5-O-tetraisopropyl-disiloxan-1,3-diyl-β-D-erythro-pentofuran-2-ulosyl)-2(1H)-pyrimidinone (5 g, 9.8 mmol) in THF (120 mL) was added. After 2 hours at 0° C. the reaction was quenched with saturated ammonium chloride, the THF was removed under reduced pressure and the product was extracted into ethyl acetate (2×200 mL). The solution was dried over MgSO₄ and concentrated to give 10.3 g of the crude product. Flash chromatography (800 g silica gel, using ethyl acetate:hexane, 1:3) gave 5.3 g (81%) of (Z)-1-[2-deoxy-2-[fluoro(phenylsulfonyl)methylene]-3,5-O-[1,1,3,3-tetrakis(1-methylethyl)-1,3-disiloxanediyl]-β-D-erythro-pentfuranosyl]-4-ethoxy-2(1H)-pyrimidinone and 560 mg (8.5%) of (E)-1-[2-Deoxy-2-[fluoro(phenylsulfonyl)methylene]3,5-O-[1,1,3,3-tetrakis(1-methylethyl)-1,3-disiloxanediyl]-β-D-erythro-pentofuranosyl]-4-ethoxy-2(1H)-pyrimidinone.

(Z) isomer $^1$H NMR (CDCl$_3$): δ0.98–1.10(m,28); 1.37(t,3); 3.94–4.02(m,2); 4.14–4.19(m,1); 4.36–4.43(q,2); 5.77–5.82(m,1); 5.88–5.91(d,1,J=7.4 Hz); 6.47(m,1); 7.45–7.67(m,5); 7.56(d,1,J=7.5Hz).

$^{19}$F NMR: δ−118.8(s).

MS (CI/isobutane) m/z 669 (MH+).

HRMS, Calculated: 669.2494; Found: 669.2483.

(E) isomer $^1$H NMR (CDCl$_3$): δ1.02–1.15(m,28); 1.33(t,3); 3.94–4.06(m,2); 4.28–4.34(m,1); 4.35–4.42(q,2); 5.83(d,1,J=7.5Hz); 5.85–5.87(m,1); 6.79–6.82(m,1);7.22(d,1,J=7.6Hz); 7.52–7.99(m,5).

$^{19}$F NMR: δ−114.95.

MS (CI/CH$_4$) m/z 669 (MH+).

(Z)-1-[2-Deoxy-2-[fluoro(tributylstannyl)methylene]-3,5-O-[1,1,3,3-tetrakis(1-methylethyl)-1,3-disiloxanediyl]-β-D-erythro-pentofuranosyl]-4-ethoxy-2(1H)-pyrimidinone: Under argon, a mixture of (Z)-1-[2-deoxy-2-[fluoro(phenylsulfonyl) methylene]-3,5-O-[1,1,3,3-tetrakis(1-methylethyl)-1,3-disiloxanediyl]-β-D-erythro-pentofuranosyl]-4-ethoxy-2(1H)-pyrimidinone (4.6 g, 6.9mmol), tributyltin hydride (6.0 g, 20.7 mmol), AIBN (400 mg) and benzene (200 mL) was heated to a gentle reflux. After 3 hours, the reaction was concentrated to give 10.6 g of crude product. The product was purified by flash chromatography (700 g silica gel, using ethyl acetate:hexane, 1:5). After concentration of the fractions containing the title compound and drying under high vacuum, 4.39 g (78%) of the title compound was obtained as a viscous colorless oil.

$^1$H NMR (CDCl$_3$): δ0.87(t,9); 0.95–1.11 (m,28); 1.21–1.47(m,18);

1.35(t,3); 3.81–3.91(m,2); 3.97–4.03(m,1); 4.40–4.47(q,2);

5.19(m,1); 5.85(d,1,J=7.4 Hz); 6.75(m,1); 7.42(d,1,J=7.5Hz).

$^{19}$F NMR: δ−92.41(s) and weak doublet centered at −92.41(J=218Hz) (splitting caused by minor isotopes of tin with spin of ½). MS (CI/CH$_4$) m/z 817 (MH+).

(E)-4-Amino-1-[2-deoxy-2-(fluoromethylene)-3,5-O-[1,1,3,3-tetrakis(1-methylethyl )-1,3-disiloxanediyl]β-D-erythro-pentofuranosyl]-2(1H)-pyrimidinone In a Carius tube was placed (Z)-1-[2-deoxy-2-[fluoro(tributylstannyl)methylene]-3,5-O-[1,1,3,3-tetrakis(1-methylethyl)-1,3-disiloxanediyl]-β-D-erythropentofuranosyl]- 4-ethoxy-2(1H)-pyrimidinone (4.0 g, 4.89 mmol) in methanol (30 mL) and the solution was cooled to 0° C. After saturation with NH$_3$, the tube was sealed and warmed to room temperature then to 50° C. After 18 hours, the product was purified by flash chromatography (500 g silica gel, CHCl$_3$:CH$_3$OH:NH$_4$OH, 90:7:0.7) to yield 2.2 g (90%) of the title compound as a colorless oil.

$^1$H NMR (CDCl$_3$): δ0.88–0.94(m,9); 1.03–1.11(m,28); 1.08–1.15(m,6); 1.28–1.38(m,6); 1.52–1.64(m,6); 3.55(m,1); 3.91(m,1):

4.04–4.08(m,2); 5.69(d,1,J=7.5 Hz); 6.80(dt,1,J=80.8, 1.9 Hz);

6.84–6.87(m,1); 6.95–6.99(m,1); 7.71(d,1,J=7.5 Hz).

$^{19}$F NMR: δ−130.04(d,J=80.4 Hz) major and −131.26(d,J=82.3 Hz) minor (possibly TIPDS group cleaved).

MS (CI/CH$_4$) m/z 500 (MH+).

(E)-4-Amino-1-[2-deoxy-2-(fluoromethylene)-β-D-erythropentofuranosyl]-2(1H)-pyrimidinone [or (E)-2'-deoxy-2'-fluoromethylidenecytidine]

A mixture of (E)-4-amino-1-[2-deoxy-2-(fluoromethylene)-3,5-O-[1,1,3,3-tetrakis(1-methylethyl)-1,3-disiloxanediyl]-β-D-erythro-pentofuranosyl]-2(1H)-pyrimidinone (2.0 g, 4 mmol), methanol (200 mL) and CsF (3.0 g, 2 mmol) was stirred overnight at room temperature. Additional CsF (9 g, 6 mmol) was added and stirring was continued for 4 days. The reaction was concentrated and purified by flash chromatography on 400 g silica gel (upper phase of ethyl acetate:n-propanol:water, 4:1:2). After drying under vacuum, 1.19 g (100%) of the title compound was obtained as a white, tacky foam. Recrystallization from 75 mL of acetonitrile gave 208 mg of the title compound as white crystals, mp 166–168° C. (foamed and turned yellow).

$^1$H NMR (DMSO-d$_6$): δ3.48–3.62(m,2); 3.73–3.78(m,1); 4.73–4.78(m,1); 4.95(t,1,J=5.6 Hz); 5.65(d,1,J=6.9 Hz);

5.73(d,1,J=7.6 Hz); 6.65–6.68(m,1); 6.77(dt,1,J=81.3, 2.0 Hz);

7.25(br/s,1); 7.54(d,1,J=7.3 Hz).

$^{13}$C NMR (CDCl$_3$): δ60.89, 68.04, 82.25 (J=10.2Hz), 86.14, 94.94, 125.39 (J=8.8 Hz), 141.72, 145.75, 149.21, 155.08, 165.58.

$^{19}$F NMR (CDCl$_3$): δ−130.05(d,J=80.9 Hz).

MS (NEG CI/CH$_4$)257 (M−·).

Analytical:

Calculated for C$_{10}$H$_{12}$FN$_3$O$_4$: C, 46.70; H, 4.70; N, 16.34

Found: C, 46.62; H, 4.75; N, 16.23.

In addition, the following compounds may be prepared using procedures and techniques analogous to that described above: (Z)-4-Amino-1-[2-deoxy-2-(fluoromethylene)-δ-D-erythropentofuranosyl]-2(1H)-pyrimidinone can be prepared from (E)-1-[2-deoxy-2-[fluoro(phenylsulfonyl)methylene]-3,5-O-[1,1,3,3-tetrakis(1-methylethyl)-1,3-disiloxanediyl]-β-D-erythro-pentofuranosyl]-4-ethoxy-2(1H)-pyrimidinone (520 mg, 0.78 mmol) in a manner analogous to that described above to yield (after flash chromatography on silica gel using upper phase of ethyl acetate:n-propanol:water (4:1:2) and recrystallization from acetonitrile) 43 mg (22%) of the (Z) isomer as a waxy, tan solid.

$^1$H NMR (DMSO-d$_6$): δ3.48–3.58(m,1); 3.60–3.70(m,2); 4.63–4.72(m,1); 4.87(t,1); 5.67(d,1); 5.72(d,1); 6.74(m,1);

6.88(dt,1); 7.22(hr d,2); 7.43(d,1).

$^{19}$F NMR (DMSO-d$_6$): δ−130.54(d,J=81 Hz).

MS (NEG CI/CH$_4$) m/z 257 (M−·).

HRMS Calc'd:258.0890; Found:258.0898.

(Z)-4-amino-1-[2-deoxy-2-(chloromethylene)-β-D-erythro-pentofuranosyl]-2(1H)-pyrimidinone can be prepared utilizing (chloromethyl)triphenylphosphonium chloride as the Wittig reagent to yield [after flash chromatography on silica gel using upper phase of ethyl acetate:n-propanol:water (4:1:2)]477 mg (58%) as a white solid (mp 110–112° C).

$^1$H NMR (DMSO-d$_6$): δ3.20–3.65(m,2); 3.66–3.74(m,1); 4.35(t,1);

4.58–4.67(m,1); 4.84(t,1); 5.70(d,1); 5.82(d,1); 6.43(s,1);

6.52(m,1); 7.22(hr d,2); 7.38(d,1).

MS (CI/CH$_4$) m/z 274(MH+), 256(MH+-H$_2$O).
HRMS Calc'd:274.0595;
Found:274.0580.

In many of the synthetic schemes presented above, the 4-ethoxy-pyrimidone derivative (2) is utilized as the starting material. It will be appreciated by those skilled in the art that the 4-ethoxy moiety can be converted, if desired, to either a keto group (to form a uridine/thymidine derivative) or to an amino group (to form a cytidine derivatives. Alternatively, where a uridine, thymidine or cytidine derivative is desired, a 2-keto starting material (2) can be utilized wherein the base moiety is cytosine, uracil or thymine.

Starting materials for use in the general synthetic procedure outlined in Schemes A through E are readily available by the use of synthetic methods and procedures which are well known and appreciated by those of ordinary skill in the art. For example, 4-ethoxy-1-[(3,5-O-tetraisopropyldisiloxan-1,3-diyl)-2-keto-β-D-erythro-pentofuranosyl]-2(1H)-pyrimidone can be used as the starting material for many of the compounds of formulas (1), (1a) and (1b) and can be prepared from uridine according to the procedure described by Matsuda et al.[Chem. Pharm. Bull. 1988, 36, 945]. 9-[(3,5-O-Tetraisopropyldisiloxan-1,3-diyl)-2-keto-β-D-erythro-pentofuranosyl]guanine can be prepared from guanosine by a procedure analogous to that described by Hansske et al. [Tetrahedron 1984, 40, 125]. Other 2-keto starting materials can be prepared by the use of methods analogous to those described by the methods described above as well as other conventional methods as are well known and appreciated in the art such as that described by Hansske and Robins [Tetrahedron Lett. 1983, 24, 1589].

In a further embodiment, the present invention provides a method for the treatment of a patient afflicted with a carcinoma comprising the administration thereto of a therapeutically effective antineoplastic amount of a compound of formula (1), (1a) or (1b). Carcinomas in vitro for which treatment with a compound of formula (1), (1a) or (1b) will be particularly useful include Carcinomas, such as, but not limited to, those of the cervix, oesophagus, stomach, small intestines, colon and lungs.

As used herein, the term "patient" refers to a warm-blooded animal, such as a human, which is afflicted with a particular carcinoma.

A therapeutically effective antineoplastic amount of a compound of formula (1), (1a) or (1b) refers to an amount which is effective, upon single or multiple dose administration to the patient, in controlling the growth of the carcinoma or in prolonging the survivability of the patient beyond that expected in the absence of such treatment. As used herein, "controlling the growth" of the carcinoma refers to slowing, interrupting, arresting or stopping its growth and metastases and does not necessarily indicate a total elimination of the carcinoma.

As used herein, the term "therapeutically effective amount" refers to a therapeutically effective antineoplastic amount of a compound of the formula (1), (1a) or (1b). A therapeutically effective amount can be readily determined by the attending diagnostician, as one skilled in the art, by the use of known techniques and by observing results obtained under analogous circumstances. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formula (1), (1a) or (1b) is expected to vary from about 0.1 milligram per kilogram of body weight per day (mg/kg/day) to about 100 mg/kg/day. Preferred amounts are expected to vary from about 0.5 to about 10 mg/kg/day.

In effecting treatment of a patient afflicted with a disease state described above, a compound of formula (1), (1a) or (1b) can be administered in any form or mode which makes the compound bioavailable in effective amounts, including oral and parenteral routes. For example, compounds of formula (1), (1a) or (1b) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formula (1), (1a) or (1b) in admixture or otherwise in association with one or more inert carriers. These compositions are useful, for example, as assay standards, as convenient means of making bulk shipments, or as pharmaceutical compositions. An assayable amount of a compound of formula (1), (1a) or (1b) is an amount which is readily measurable by standard assay procedures and techniques as are well known and appreciated by those skilled in the art. Assayable amounts of a compound of formula (1), (1a) or (1b) will generally vary from about 0.001% to about 75% of the composition by weight. Inert carriers can be any material which does not degrade or otherwise covalently react with a compound of formula (1), (1a) or (1b). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula (1), (1a) or (1b) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0-300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (1), (1a) or (1b) in their end-use application.

With respect to the substituents $X_1$ and $X_2$, compounds of formula (1) wherein $X_1$ is fluoro and $X_2$ is hydrogen, and those wherein $X_1$ is hydrogen and $X_2$ is fluoro, are generally preferred.

With respect to the substituent R, compounds of the formulas (1a) and (1b) wherein R is hydrogen are generally preferred.

The following are additional preferred embodiments for compounds of formula (1), (1a) or (1b): compounds wherein V is oxy, compounds wherein $Y_1$ is a CH group, compounds wherein $Y_2$ is nitrogen, compounds wherein $Y_3$ is nitrogen and compounds wherein Z is hydrogen are generally preferred.

The following list identifies compounds of the formula (1), (1a) and (1b) which are particularly preferred embodiments of the present invention:

2'-deoxy-2'-difluoromethylidene-cytidine
2'-deoxy-2'-difluoromethylidene-uridine
2'-deoxy-2'-difluoromethylidene-guanosine
(Z) and (E) 2'-deoxy-2'-fluoromethylidene-cytidine
(Z) and (E) 2'-deoxy-2'-fluoromethylidene-uridine
(Z) and (E) 2'-deoxy-2'-fluoromethylidene-guanosine
2'-deoxy-2'-ethenylidene-cytidine
2'-deoxy-2'-ethenylidene-uridine
2'-deoxy-2'-ethenylidene-guanosine
2'-deoxy-2'(R) and (S)-ethynyl-cytidine
2'-deoxy-2'(R) and (S)-ethynyl-uridine
2'-deoxy-2'(R) and (S)-ethynyl-guanosine.

The following example provides an illustration of the utility of the compounds of the present invention. This example is understood to be illustrative only and is not intended to limit the scope of the invention in any way.

EXAMPLE 14

INHIBITORY EFFECTS OF COMPOUNDS ON HeLa CELL PROLIFERATION

The inhibitory effect of various compounds of formula (1) on HeLa cell proliferation in vitro was determined according to the method described by Sunkara et al. [*J. Natl. Cancer Instit.* 70, 505–509 (1983)]. Exponentially growing HeLa cells were incubated in the presence or absence of various concentrations of test compounds for 96 hours. $IC_{50}$ values were calculated which represent the test compound concentration at 50% inhibition of cell growth. The results of this study are presented in Table 1.

TABLE 1

| INHIBITORY EFFECTS OF COMPOUNDS ON HeLa CELL PROLIFERATION | |
|---|---|
| Compound | Growth Inhibition $IC_{50}$, $\eta$g/mL |
| A | 10–15 |
| B | 1000–5000 |

Compound A = (E)-2'-deoxy-2'-fluoromethylidene cytidine
Compound B = (Z)-2'-deoxy-2'-fluoromethylidene cytidine.

We claim:
1. A compound of the formula

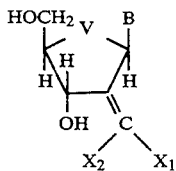

wherein

V is oxy, $X_1$ and $X_2$ are each independently hydrogen or halogen, with the proviso that at least one of $X_1$ and $X_2$ is halogen, B is a radical of the formula

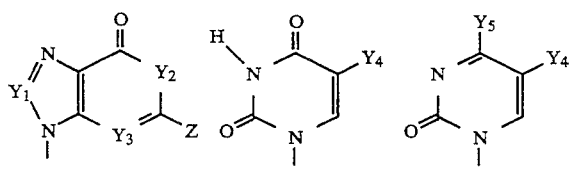

wherein $Y_1$ is a CH group; $Y_2$ is an NH group; $Y_3$ is a nitrogen; $Y_4$ is hydrogen; $Y_5$ is amino; and Z is $NH_2$;

or a pharmaceutically acceptable salt thereof.

2. A compound of claim 1 wherein $X_1$ is fluoro and $X_2$ is hydrogen.

3. A compound of claim 1 wherein $X_1$ is hydrogen and $X_2$ is fluoro.

4. A compound of claim 1, wherein $Y_1$ is a CH group.

5. A compound of claim 1, wherein $Y_2$ is nitrogen.

6. A compound of claim 1, wherein $Y_3$ is nitrogen.

7. A pharmaceutical composition comprising a therapeutically effective amount of a compound of claim 1, in admixture or otherwise in association with one or more pharmaceutically acceptable carriers or excipients.

8. A compound of claim 1 wherein the compound is 2'-deoxy-2'-difluoromethylidene-cytidine.

9. The compound of claim 1 wherein the compound is 2'-deoxy-2'-difluoromethylidene-uridine.

10. The compound of claim 1 wherein the compound is 2'-deoxy-2'-difluoromethylidene-guanosine.

11. A compound of claim 1 wherein the compound is (E)-2'-deoxy-2'-fluoromethylidene-cytidine.

12. A compound of claim 1 wherein the compound is (Z)-2'-deoxy-2'-fluoromethylidene-cytidine.

13. A compound of claim 1 wherein the compound is (Z) or (E)-2'-deoxy-2'-fluoromethylidene-uridine.

14. A compound of claim 1 wherein the compound is (Z) or (E) 2'-deoxy-2'-fluoromethylidene-guanosine.

* * * * *

UNITED STATES PATENT AND TRADEMARK OFFICE
CERTIFICATE OF CORRECTION

PATENT NO. : 5,378,693

DATED : January 3, 1995

INVENTOR(s) : James R. McCarthy; Michael L. Edwards; Donald P. Matthews

It is certified that error appears in the above-identified patent and that said Letters Patent is hereby corrected as shown below:

Column 3, Line 10, Scheme A Patent reads "($X_{HAL}$)($SO_2Ar$) and should read --($X_{HAL}$)($X_{HAL}$--.

Column 6, Line 5 Patent reads "4-Ethoxy-1,[(3,5-O-" and should read -- 4-Ethoxy-1-[(3,5-O- --.

Column 13, Line 17 Patent reads "2(erthyro-pentofuran-2-" and should read --2-(ethenylidene)osyl]- --.

Column 13, Line 47 Patent reads "1-[3,5-" and should read --1-[(3,5- --.

Column 15, Line 46 Patent reads "tetraisopropryldisiloxan" and should read --tetraisopropyldisiloxan--

Column 15, Line 57 Patent reads "ice bath Add" and should read --ice bath (0°C). Add--.

Column 17, Line 39 Patent reads "C($X_{HAL}$)----->" and should read --CH($X_{HAL}$)---->--.

Column 20, Line 6 Patent reads "ß0.98" and should read --δ0.98--.

Column 20, Line 14 Patent reads "(E)-1) and should read --(E)-1- --.

Column 21, Line 2 Patent reads "pentfuranosyl" and should read --pentofuranosyl--.

Column 21, Line 9 Patent reads "60.98" and should read --δ0.98--.

Column 21, Line 50 Patent reads "]ß-D-" and should read --]-ß-D- --.

Column 22, Line 40 Patent reads "-δ-D-" and should read -- -ß-D- --.

Signed and Sealed this

Seventeenth Day of November, 1998

BRUCE LEHMAN

Attest:

Attesting Officer

Commissioner of Patents and Trademarks